(12) United States Patent
McMorrow et al.

(10) Patent No.: US 11,530,910 B2
(45) Date of Patent: Dec. 20, 2022

(54) FORWARD LOOKING RGB/OPTICAL COHERENCE TOMOGRAPHY DUPLEX IMAGER

(71) Applicant: VerAvanti Inc., Redmond, WA (US)

(72) Inventors: Gerald McMorrow, Redmond, WA (US); Jongtae Yuk, Redmond, WA (US)

(73) Assignee: VERAVANTI INC., Redmond, WA (US)

( * ) Notice: Subject to any disclaimer, the term of this patent is extended or adjusted under 35 U.S.C. 154(b) by 57 days.

(21) Appl. No.: 17/236,901

(22) Filed: Apr. 21, 2021

(65) Prior Publication Data

US 2021/0239451 A1    Aug. 5, 2021

Related U.S. Application Data

(62) Division of application No. 16/777,807, filed on Jan. 30, 2020, now Pat. No. 11,047,671.

(51) Int. Cl.
| | | |
|---|---|---|
| *G01B 9/02091* | (2022.01) | |
| *A61B 3/10* | (2006.01) | |
| *A61B 1/00* | (2006.01) | |
| *A61B 90/00* | (2016.01) | |

(52) U.S. Cl.
CPC ........ *G01B 9/02091* (2013.01); *A61B 1/0005* (2013.01); *A61B 1/0017* (2013.01); *A61B 3/102* (2013.01); *A61B 2090/3735* (2016.02); *G01B 2290/65* (2013.01)

(58) Field of Classification Search
CPC ............ G01B 9/02091; G01B 2290/65; G01B 9/0203; G01B 9/02087; A61B 1/0017; A61B 3/102; A61B 2090/3735; A61B 1/0005; A61B 1/00172; A61B 5/0066; A61B 5/0084
See application file for complete search history.

(56) References Cited

U.S. PATENT DOCUMENTS

| | | |
|---|---|---|
| 6,294,775 B1 | 9/2001 | Seibel et al. |
| 6,563,105 B2 | 5/2003 | Seibel et al. |
| 6,845,190 B1 | 1/2005 | Smithwick et al. |
| 6,856,712 B2 | 2/2005 | Fauver et al. |
| 6,959,130 B2 | 10/2005 | Fauver et al. |

(Continued)

FOREIGN PATENT DOCUMENTS

| | | |
|---|---|---|
| AU | 2002331723 B2 | 3/2007 |
| CN | 1310615 C | 4/2007 |

(Continued)

OTHER PUBLICATIONS

U.S. Appl. No. 11/833,831, filed Aug. 3, 2007, Johnston et al.

(Continued)

*Primary Examiner* — Michael P LaPage
(74) *Attorney, Agent, or Firm* — BakerHostetler (57) ABSTRACT

Systems, methods, and devices for directed to duplex imaging techniques for combining high-resolution surface images obtained with a Scanning Fiber Endoscope (SFE), and high-resolution penetrating OCT images obtained through Optical Coherence Tomography (OCT), from a SFE, and interleaving frames to improve resolution and identify below surface information of biological structures.

17 Claims, 9 Drawing Sheets

(56) References Cited

U.S. PATENT DOCUMENTS

| | | | |
|---|---|---|---|
| 6,975,898 | B2 | 12/2005 | Seibel |
| 7,068,878 | B2 | 6/2006 | Crossman-Bosworth et al. |
| 7,159,782 | B2 | 1/2007 | Johnston et al. |
| 7,189,961 | B2 | 3/2007 | Johnston et al. |
| 7,252,236 | B2 | 8/2007 | Johnston et al. |
| 7,298,938 | B2 | 11/2007 | Johnston |
| 7,312,879 | B2 | 12/2007 | Johnston et al. |
| 7,349,098 | B2 | 3/2008 | Li |
| 7,391,013 | B2 | 6/2008 | Johnston et al. |
| 7,395,967 | B2 | 7/2008 | Melville |
| 7,447,415 | B2 | 11/2008 | Melville et al. |
| 7,522,813 | B1 | 4/2009 | Johnston et al. |
| 7,583,872 | B2 | 9/2009 | Seibel et al. |
| 7,608,842 | B2 | 10/2009 | Johnston |
| 7,616,986 | B2 | 11/2009 | Seibel et al. |
| 7,680,373 | B2 | 3/2010 | Melville et al. |
| 7,738,762 | B2 | 6/2010 | Melville et al. |
| 7,784,697 | B2 | 8/2010 | Johnston et al. |
| 7,791,009 | B2 | 9/2010 | Johnston et al. |
| 7,813,538 | B2 | 10/2010 | Carroll et al. |
| 7,901,348 | B2 | 3/2011 | Soper et al. |
| 8,212,884 | B2 | 7/2012 | Seibel et al. |
| 8,305,432 | B2 | 11/2012 | Johnston |
| 8,382,662 | B2 | 2/2013 | Soper et al. |
| 8,411,922 | B2 | 4/2013 | Lee et al. |
| 8,437,587 | B2 | 5/2013 | Melville |
| 8,466,956 | B2 * | 6/2013 | Sugimoto ............. H04N 9/097 600/478 |
| 8,537,203 | B2 | 9/2013 | Seibel et al. |
| 8,840,566 | B2 | 9/2014 | Seibel et al. |
| 8,929,688 | B2 | 1/2015 | Johnston |
| 8,957,484 | B2 | 2/2015 | Melville et al. |
| 9,066,651 | B2 | 6/2015 | Johnston |
| 9,160,945 | B2 | 10/2015 | Johnston |
| 9,226,687 | B2 | 1/2016 | Soper et al. |
| 9,554,729 | B2 | 1/2017 | Soper et al. |
| 9,561,078 | B2 | 2/2017 | Seibel et al. |
| 10,080,484 | B2 | 9/2018 | Yang et al. |
| 2001/0055462 | A1 | 12/2001 | Seibel |
| 2002/0139920 | A1 | 10/2002 | Seibel et al. |
| 2006/0170930 | A1 | 8/2006 | Li |
| 2008/0058629 | A1 | 3/2008 | Seibel et al. |
| 2008/0144998 | A1 | 6/2008 | Melville et al. |
| 2008/0161648 | A1 | 7/2008 | Karasawa |
| 2008/0165360 | A1 | 7/2008 | Johnston |
| 2009/0137893 | A1 | 5/2009 | Seibel et al. |
| 2013/0271757 | A1 | 10/2013 | Kang et al. |
| 2018/0196250 | A1 * | 7/2018 | Shimamoto ............. G02B 23/26 |
| 2018/0315194 | A1 | 11/2018 | Moult et al. |
| 2020/0273216 | A1 | 8/2020 | Kennedy et al. |

FOREIGN PATENT DOCUMENTS

| | | | |
|---|---|---|---|
| EP | 1803008 | A1 | 7/2007 |
| EP | 1805779 | A1 | 7/2007 |
| EP | 1851673 | A1 | 11/2007 |
| EP | 1954193 | A1 | 8/2008 |
| EP | 2061367 | A1 | 5/2009 |
| EP | 2096688 | A2 | 9/2009 |
| EP | 2224841 | A1 | 9/2010 |
| EP | 2225699 | A1 | 9/2010 |
| EP | 1592992 | B1 | 5/2012 |
| EP | 1691666 | B1 | 5/2012 |
| EP | 2653995 | A1 | 10/2013 |
| EP | 2179454 | B1 | 1/2016 |
| EP | 2099353 | B1 | 9/2018 |
| EP | 2092388 | B1 | 10/2018 |
| EP | 3415075 | A1 | 12/2018 |
| EP | 3552534 | A2 | 10/2019 |
| JP | 4080426 | B2 | 4/2008 |
| JP | 2009-212519 | A | 9/2009 |
| JP | 2011-504782 | A | 2/2011 |
| JP | 2011-504783 | A | 2/2011 |
| JP | 4672023 | B2 | 4/2011 |
| JP | 5025877 | B2 | 9/2012 |
| JP | 5069105 | B2 | 11/2012 |
| JP | 5069310 | B2 | 11/2012 |
| JP | 5097270 | B2 | 12/2012 |
| JP | 5190267 | B2 | 4/2013 |
| JP | 5513897 | B2 | 6/2014 |
| JP | 5608718 | B2 | 10/2014 |
| JP | 5781269 | B2 | 9/2015 |
| WO | WO 2001/097902 | A3 | 12/2001 |
| WO | WO 2003/019661 | A1 | 3/2003 |
| WO | WO 2004/068218 | A2 | 8/2004 |
| WO | WO 2005/058137 | A2 | 6/2005 |
| WO | WO 2006/004743 | A2 | 1/2006 |
| WO | WO 2006/041452 | A1 | 4/2006 |
| WO | WO 2006/041459 | A1 | 4/2006 |
| WO | WO 2006/071216 | A1 | 7/2006 |
| WO | WO 2006/096155 | A1 | 9/2006 |
| WO | WO 2007/067163 | A1 | 6/2007 |
| WO | WO 2007/106075 | A2 | 9/2007 |
| WO | WO 2008/033168 | A1 | 3/2008 |
| WO | WO 2008/076149 | A1 | 6/2008 |
| WO | WO 2008/085186 | A1 | 7/2008 |
| WO | WO 2009/014525 | A1 | 1/2009 |
| WO | WO 2009/070160 | A1 | 6/2009 |
| WO | WO 2009/070161 | A1 | 6/2009 |
| WO | WO 2019/071295 | A1 | 4/2019 |

OTHER PUBLICATIONS

U.S. Appl. No. 60/138,404, filed Jun. 8, 1999, Seibel.
U.S. Appl. No. 60/212,411, filed Jun. 19, 2000, Seibel.
U.S. Appl. No. 60/253,445, filed Nov. 27, 2000, Seibel et al.
U.S. Appl. No. 60/333,421, filed Nov. 26, 2001, Seibel et al.
U.S. Appl. No. 60/442,852, filed Jan. 24, 2003, Seibel et al.
U.S. Appl. No. 60/529,077, filed Dec. 12, 2003, Seibel et al.
U.S. Appl. No. 60/644,335, filed Jan. 14, 2005, Li
U.S. Appl. No. 60/912,237, filed Apr. 17, 2007, Carroll et al.
U.S. Appl. No. 61/589,069, filed Jan. 20, 2012, N/A.
U.S. Appl. No. 61/934,479, filed Jan. 31, 2014, Yang et al.
International Patent Application No. PCT/2021/14972; Invitation to Pay Add'l Fees; dated Mar. 9, 2021; 2 pages.

* cited by examiner

FIG. 1(b) Penetrating Scan

FIG. 1(a) RGB Surface Scan

FIG. 1(c) RGB Surface Scan and Penetrating Scan

FIG. 4(b) Reconstructed Slices

FIG. 4(a) Acquired Planes

FIG. 5(b) Simulated compounding image

FIG. 5(a) Original OCT Image

FORWARD LOOKING RGB/OPTICAL COHERENCE TOMOGRAPHY DUPLEX IMAGER

CROSS REFERENCE TO RELATED APPLICATIONS

This application is a divisional of U.S. patent application Ser. No. 16/777,807, filed Jan. 30, 2020, the contents of which is incorporated herein by reference in its entirety.

BACKGROUND

Chronic Total Occlusion (CTO) refers to a complete obstruction of the coronary artery. CTOs can result from coronary artery disease and develop due to atherosclerosis. The blockage prevents all downstream blood flow, and can cause a range of symptoms and issues, including chest pain and heart attacks. In some patients, however, CTOs cause no physically identifiable symptoms, e.g., silent heart attacks, and the CTOs go undiagnosed. Many patients with CTO also do not receive therapy due to practical difficulties of penetrating the occlusion with partially complete angiographic images.

Intravascular Ultrasound (IVUS) and Optical Coherence Tomography (OCT) are two current methods for intercoronary imaging. IVUS traditionally utilizes a catheter with an ultrasound probe on a proximal end and provides a cross-sectional view of blood vessels. OCT operates similarly but utilizes the longitudinal partial coherence of light rather than time delay of sound waves, to obtain information from reflected, scattered light. OCT can provide resolution on the order of micrometers, but its penetration depth is often limited to several millimeters below tissue surface. Both IVUS and OCT provide only a radial visualization at the imaging location. This requires the imaging device to pass by the occlusion to image it. When applied to arterial imaging and diagnosing CTO's, for example, these techniques can provide cross-sectional information of the vessel, such as, indications of narrowing in the artery, e.g., due to plaque build-up, but cannot provide information beyond the position of their side scanning sensors within the vessel. Therefore, when a CTO or other blockage is present, current IVUS and OCT probes must penetrate the occlusion before any CTO visualization is possible.

Penetration of the occlusion is often the blocking step to being able to complete therapy such as placing a stent. Penetration with a guidewire, for example, can be very time-consuming, e.g., 30 minutes or more, and in some cases, penetration is not possible. Accidentally exiting the lumen with the guidewire poses an additional risk, as doing so can cause significant damage to the patient. As such, it would be advantageous to have the ability to identify and visualize an occlusion prior to and during the penetration procedure.

Scanning Fiber Endoscopes (SFE) can provide color imaging based on RGB reflectance, and wide-field viewing of the internal arterial region and proximal CTO. SFE imaging techniques only provide surface information within the artery and of the proximal end of the CTO. The invention herein combines forward looking RGB reflectance images combined with forward penetrating sectional images of CTO using OCT.

SFE probes scan at approximately 10 kHz for RGB imaging, which provides a single revolution time of about 100 μs. This rotation leaves little time for any OCT scan. Scanning with OCT while changing the location of the scan this quickly would cause the OCT image to be useless from excessive lateral motion artifact. OCT imagers require 7-8 μs imaging time per line and deliver a 100 kHz A-line acquisition speed. At this rate, during one spiral rotation, only 10 A-line samples can be obtained, thus resulting in poor OCT lateral resolution due to probe movement artifact during the wavelength-sweep and a lack of A-lines to compose the penetrating B-mode image. To reduce the rotational speed of the SFE probe, significant modifications are required to be made, e.g., changing the length of fiber inside the SFE, but such changes are often not adequate for RGB imaging, causing slow frame rates and larger rigid length of the RGB imager.

SUMMARY

Systems, methods, and devices for improving Forward looking OCT imaging techniques combined with forward looking SFE surface images. The present technology can provide a forward viewing direction, useful for various medical applications and identifying cross-sectional information of biological structures, such as Chronic Total Occlusions.

In embodiments, systems and methods can comprise a probe for RGB surface imaging and optical coherence tomography (e.g., a scanning fiber endoscope), the probe being electronically configured to obtain (1) frames of surface images, and (2) orthogonal penetrating images along an image plane defined by a line on the surface image. At least one computing device can be operable to obtain A-line scans at a plurality of points along the scanning path where a speed of the probe is at a minimum and to construct at least one frame having B-mode images from the plurality of A-line scans.

In various embodiments, a plurality of B-mode images offset by a scanning angle can be compiled and interleaved to construct three-dimensional images.

As discussed herein, the present invention can be applied to various medical applications, including but not limited to scanning and imaging within a blood vessel lumen to identify at least one of an occlusion, a defect within an occlusion, a calcification, adventitia, a microchannel, or other features within a vessel or the body.

BRIEF DESCRIPTION OF THE DRAWINGS

The combination of the two imaging modalities and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings.

In the drawings.

DETAILED DESCRIPTION OF ILLUSTRATIVE EMBODIMENTS

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of the present disclosure.

The present disclosure relates to duplex imaging techniques. More particularly, the present disclosure combines high-resolution surface images obtained with SFE, and high-resolution penetrating OCT images obtained through Optical Coherence Tomography (OCT), from a Scanning Fiber Endoscope (SFE), and interleaving frames to improve resolution and identify below surface information of biological structures. As applied to CTOs, SFE high resolution color imaging technology combined with forward-looking OCT, allows visualization of occlusions, and visualization below the surface of the occlusion prior to penetration. In addition, micro channels, calcifications, and adventitia can be imaged to provide additional clinical benefits and information. With the forward-looking imaging, a physician can, for example, identify and more safely penetrate the CTO, using a guidewire or other means, and identify a CTO's location and strong or weak aspects (calcification or microchannels) prior to penetration. Aspects of the invention further provide the ability to acquire three-dimensional (3D) OCT data. Thus, combining SFE and interleaved frames of an OCT can provide a forward viewing direction and cross-sectional information of the CTO.

The present invention can utilize certain OCT A-line acquisitions to construct frames of compounded B-mode images to identify a subsurface tissue information. FIG. 1(b), for example, identifies possible B-mode scanning angles, as indicated on a Cartesian plane with the straight lines, each input can be represented by a sinusoidal wave, and the phase difference between the inputs control the motion of imaging scans, which are typically linear. Note that OCT images are gathered only when the linear scan reaches the maximum amplitude and minimum velocity, this allows excellent OCT lateral resolution. This slow motion is like the momentary lack of motion when a child's swing reaches max height and reverses direction.

Figure 1A:
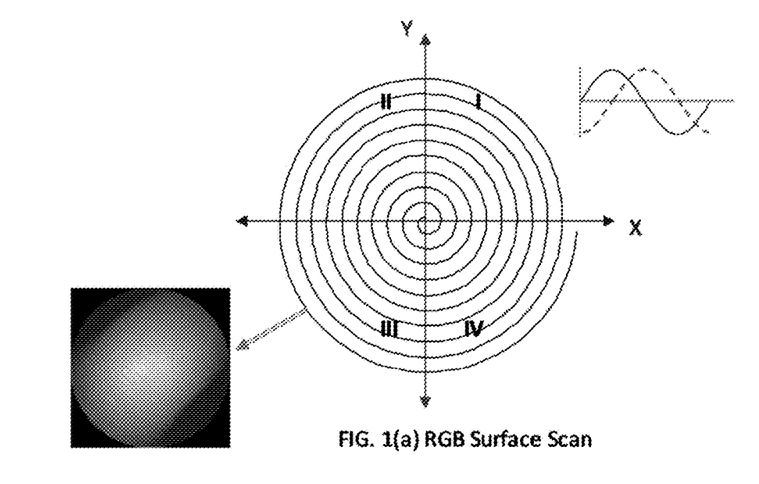
FIG. 1(a) illustrates a forward looking SFE image with an RGB image of a human finger shown in the inset.
Figure 1B:
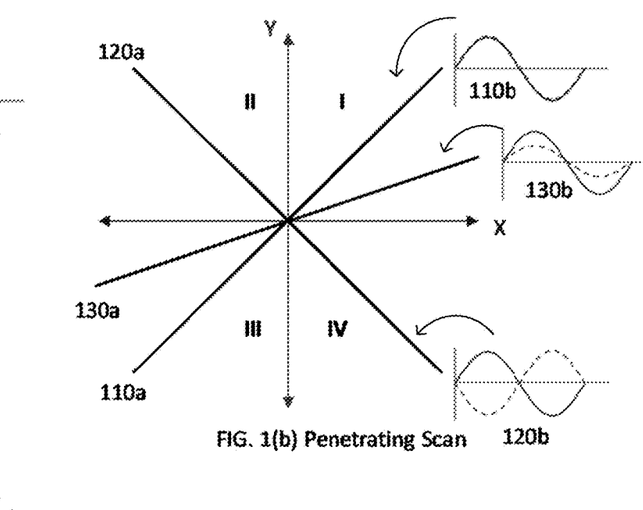
FIG. 1(b) illustrates several line scans where, using methods described herein, OCT penetrating image of a cross-sectional "cutaway image" can be displayed. Thus, the system herein can scan with a spiral raster scan or can scan with line scans as shown in FIG. 1(b).

There are also frames of spiral surface mode scans depicted in FIG. 1. These form a raster scan to scan the surface of the scene in front of it. Note that the surface speed of the scanning is very high and would "smear" the OCT scans, thus the spiral scan is used for OCT only.

Moreover, by combining B-mode scans from various rotational angles, a cone-shaped three-dimensional image can be obtained. The 3D data can be visualized in the form of multiple B-mode images acquired or reconstructed from various directions and angles.

FIG. 1(b) illustrates these principles and B-mode scanning angles with respect to a cartesian coordinate plane. Based on the relative angles between two inputs (X and Y) to the OCT probe, the overall probe motion will vary. The cartesian plane and lines 110, 120, 130 (as more fully described herein) are indicative of the probe's scanning angle with respect to a top surface of an OCT image. In other words, the two inputs X and Y represent an oscillating movement of the probe with respect to the imaging plane. The relationship between X and Y indicates the overall scanning motion, which can result in imaging of a particular area in a potential OCT field of view.

In a first example, FIG. 1(a) illustrates a forward looking SFE image of the surfaces of the anatomy facing the imaging SFE catheter. A spiral raster scan may be used to bend the SFE fiber using a cantilever resonance of the fiber stub within the SFE imager. An RGB image of a human finger, as an example of the anatomy that can be imaged, from an actual imager is shown in the inset. In the spiral surface scan mode of FIG. 1(a), two orthogonal sinusoidal waves, X and Y, with the same frequency, e.g., $\sin(2\pi ft)$ and $\cos(2\pi ft)$, can create a circular motion for imaging if the phase differences of the sinusoidal waves are 90° or $\pi/2$ radians.

In another example shown in FIG. 1(b), OCT Penetrating Scan Mode 110a, the phase difference is 0°, i.e., the phase for each input is the same, then the circular motion becomes a linear motion, as illustrated by line 110a in Quadrants I and III, and the corresponding graph 110b when X=Y. The angle is controlled via relative amplitude. The 130a and 110a scans differ only in amplitude, same phase.

In another example shown in FIG. 1(b), OCT Penetrating Scan Mode 120a, a phase difference of 180° or $\pi$ radians between each input, X and Y, also results in the scanning motion becoming linear, as represented by line 120a in Quadrants II and IV, and corresponding graph 120b. In particular, graph 120b illustrates a relationship wherein X=−Y. Here, similar to the example of line 110a and graph 110b, the scanning motion is linear, but in the opposite direction and in opposite Quadrants. Scan angles are controlled by amplitude; the same phase shown is equal amplitudes.

Figure 1C:
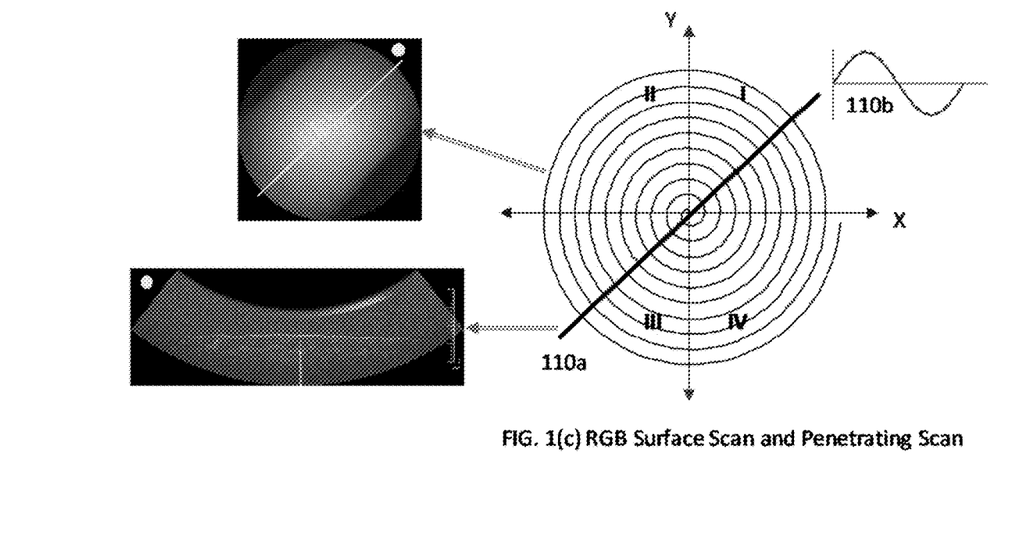
FIG. 1(c) illustrates a cross-sectional image plane that can be selected electronically relative to the RGB surface image.

FIG. 1(c) illustrates one such cross-sectional image plane that can be selected electronically relative to the RGB surface image, with the various scanning angles graphed on a Cartesian plane. The straight lines depict planes of penetrating OCT images that are possible, the spiral depicts the raster scan for the RGB surface image. These two image modalities occur by sharing frames in the 30 frame per second system disclosed herein. In effect one can have the RGB image and several planes of OCT "into the occlusion" images simultaneously. One could have 28 frames of RGB and 2 separate OCT "cutaway" images per second. The resultant user image pair is illustrated in the insets.

Figure 2:
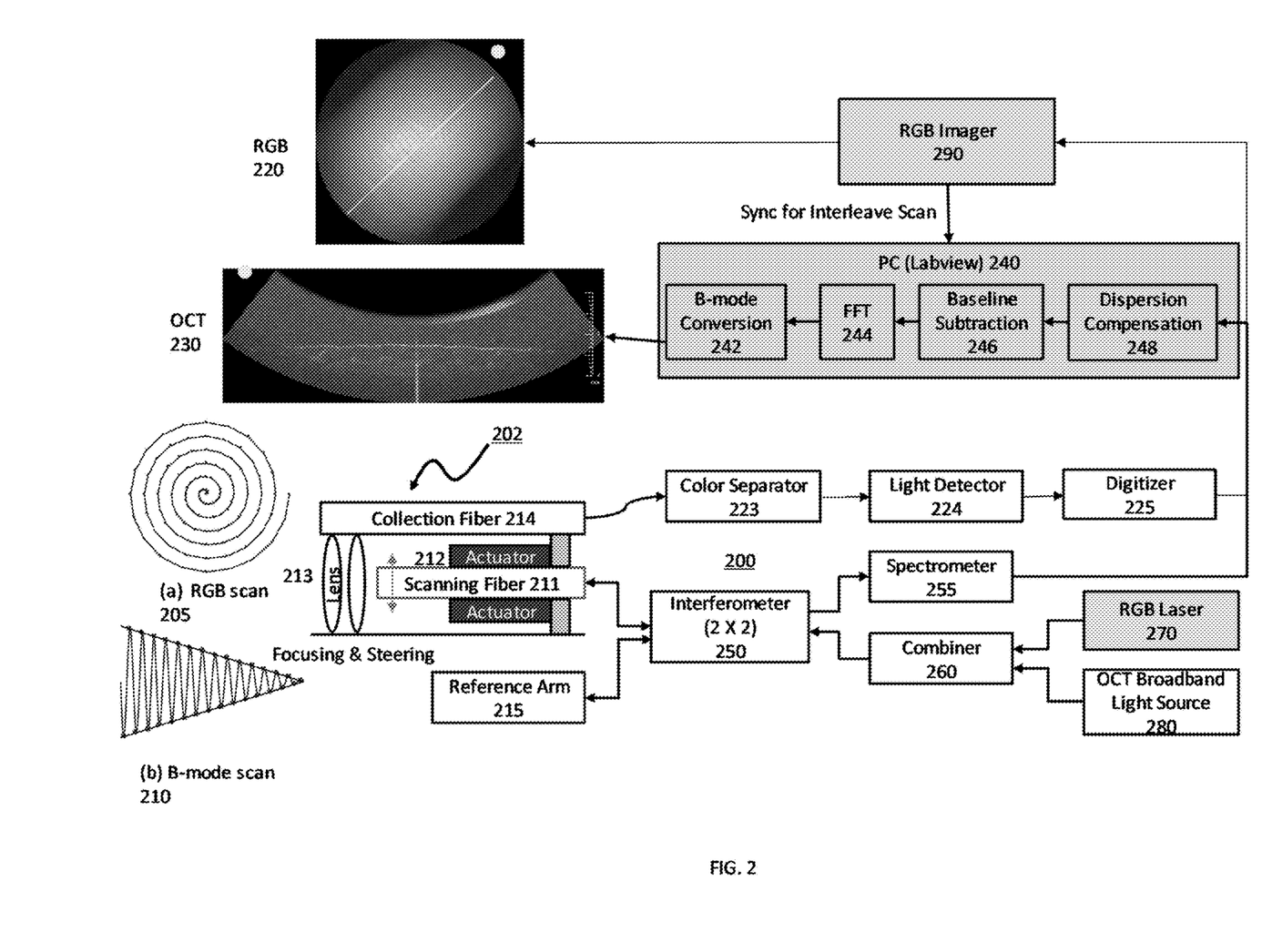
FIG. 2 illustrates a block diagram of a duplex imager capable of RGB surface images and OCT penetrating images in accordance with embodiments described herein.

FIG. 2 illustrates a block diagram of an example duplex imaging system 200 usable with one or more embodiments discussed herein. The diagram illustrates a scanning probe 202, such as an SFE, alternately performing both RGB scans 205 and penetrating B-mode scans 210, along the linear line indicated on the RGB image 220. The B-mode scan 210 along the linear line comprises collecting a plurality of A-mode information obtained at the oscillation endpoints of the scan (See also FIG. 6). The collected information from the B-mode scan may be processed through one or more computing devices (e.g., PC 240), interferometers (e.g., interferometer 250), and spectrometers (e.g., spectrometer 255) to produce the OCT image 230. The RGB scan 205 produces the RGB surface image 220, which is created from RGB reflected light through the collection fiber 214 of the scanning probe 202. The RGB surface image is processed by color separator 223, light detector 224, and digitizer 225 and input to the RGB imager 290.

A plurality of OCT images obtained from linear scans taken at various angles at the imaging location can be used to produce, a three-dimensional image, and/or information related to a forward-facing view from the end of the SFE.

In examples, surface-mode scans may be obtained from a spiral scanning fiber. As illustrated in FIG. 2, the scanning probe 202 may comprise an oscillating scanning fiber 211 activated by one or more actuators 212, one or more lenses 213 through which emitted light may be directed and focused, and the collection fiber 214 to receive reflected light for analysis. RGB light is able to propagate through the interferometer unaffected.

In OCT mode, the collected light may be first analyzed by at least one interferometer 250, which can help identify an origin and location of reflected light. In embodiments, a reference arm 215 may be utilized to provide a reference point for the interferometer 250, and additional components/systems such as an RGB laser 270, OCT Broadband Light Source 280, and combiner 260 can further contribute towards the interferometer's function.

From there, interferometer data, and additional spectrometer 255 data may be passed to the computing system 240, which may comprise one or more computing devices to perform additional processing with regard to each obtained OCT image. Processing at PC 240 may comprise a B-mode conversion module 242, Fast Fourier Transforms (FFT) 244, a baseline subtraction module 246 and a dispersion compensation 248. This processing can produce an OCT image 230.

Figure 3:
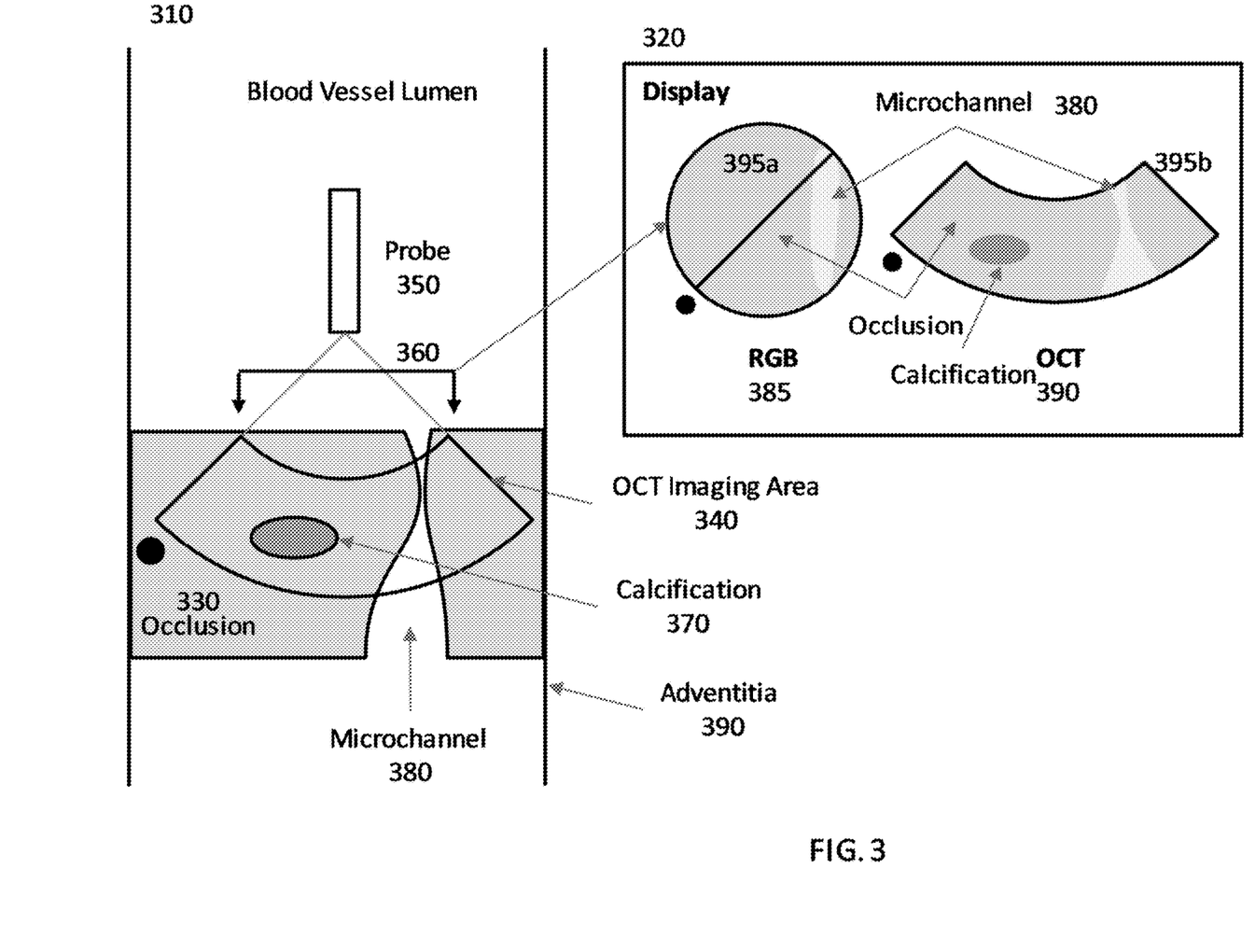
FIG. 3 illustrates a duplex image system inserted into a lumen 310. Display 320 illustrates duplex imager having RGB surface image and OCT penetrating image of a CTO 330.

FIG. 3 illustrates an example imaging operation within a blood vessel which may utilize the B-Mode imaging system 200. FIG. 3 illustrates a side view of a blood vessel lumen 310 containing an occlusion 330, an OCT scanning/imaging area 340, RGB scanned surface 360, and a display 320 of the RGB SFE and OCT scanned area. A scanning probe 350, which may comprise an oscillating scanning fiber as described herein, scans between width 360 to provide a forward-looking view within the blood vessel. As discussed herein, this forward view, e.g., along the length of the lumen, of the RGB image 360 and the penetrating view of 340 can allow observation of the surface of an occlusion 385 and a penetrating view of the occlusion 390 prior to or during contact or penetration.

In the present example, the occlusion 330 contains a calcification 370 and a microchannel 380 running through the occlusion. These features may be identified in the display section 320, which illustrates an RGB surface image 385 and a corresponding penetrating OCT image 390 along a scanning line 395a. The OCT image 390 may permit observation of a first view of the occlusion 330 which likely depicts subsurface microchannel 380 as well as the calcification 370. The RGB image 385 permits a surface view of the occlusion 385. In other words, RGB images 385 combined with OCT subsurface images 390 are forward-facing and can therefore characterize and guide therapy upon occlusion 330 and other surface and subsurface features, e.g., microchannel 380, within the viewable area in a manner not possible with either image alone.

OCT subsurface images are be obtained from a linear scanning motion. Each linear scan produces a fan-shaped OCT image 390, which can provide depth information, and be usable to identify one or more features beyond or within occlusions, blockages, and areas beyond surface-level features. The resulting B-mode image targets comprise a plurality of A-lines orthogonal to the scanning path and typically have a fan shape since the origin of the scanning probe 350 and its light point is a single point oscillating between width 360. The imaging depth in the fan-shaped B-mode can be determined by one or more variables in the OCT scanning scheme, including but not limited to reference arm length, swept-source bandwidth, and wavelength resolution.

Multiple linear penetrating OCT scans may be obtained at various angles across the circular RGB image scanning area. For example, the illustrated linear scan line 395a corresponds to the end view of the image plane of OCT image 390. The scans along line 395a produce OCT image 390, which may contain information indicative of the occlusion 330, calcification 370, and microchannel 380. Subsequent linear scans may be obtained at the operator's command to the software, with each scan line being rotated around a central point in the viewing area 360.

Figure 4A:
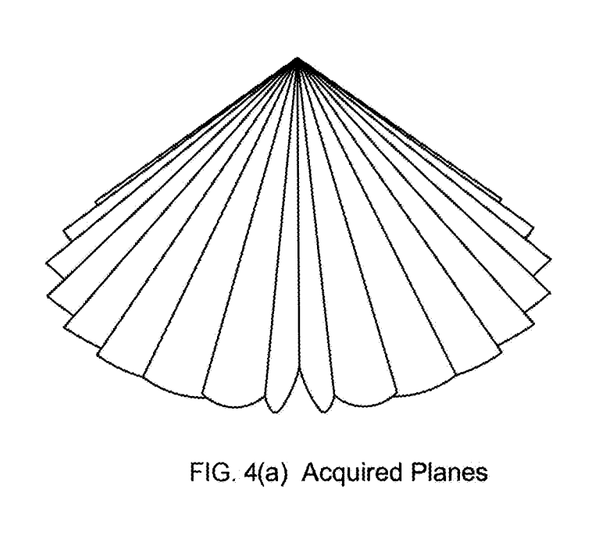
FIGS. 4(a) and 4(b) illustrate two methods of constructing three-dimensional images from the OCT penetrating image frames, with FIG. 4(a) illustrating a method using acquired planes, and FIG. 4(b) illustrating a method using reconstructed slices.

By composing the scanning patterns from various angles, three-dimensional images can be acquired. For example, using the various angles, i.e., 0° to 180°, and scanning at intervals. If 15° intervals are utilized, for example, twelve image planes can be obtained. FIG. 4(a) illustrates this concept by generating three-dimensional data from a plurality of acquired linear planes. Since each obtained A-line information contains information along the light source path, the image has path-dependency. That is, the images are affected by the reflection of layers on the line of sight, and such data provides information to identify the object structure from the image. In medical applications, for example the three-dimensional object structure can provide valuable information to a clinician, such as volume of a region. Additionally, a volumetric survey of the CTO can be performed to allow the interventionalist to select the optimum crossing technique.

Figure 4B:
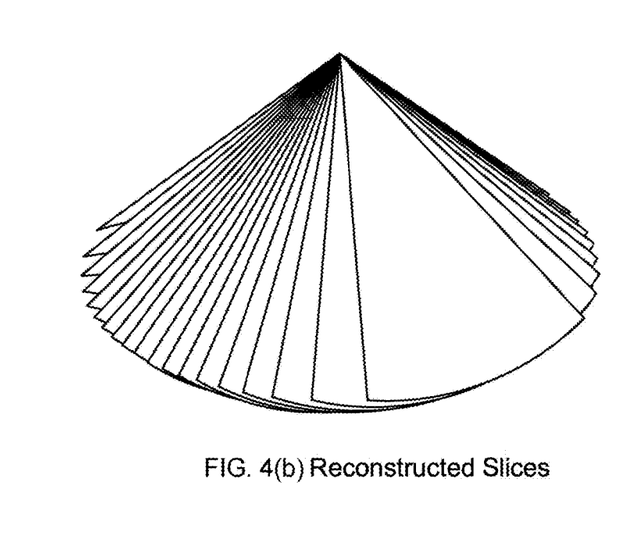

In another example, illustrated in FIG. 4(b), two-dimensional image slices having path-dependency can be reconstructed to acquire the three-dimensional structure. The sliced B-mode images can be obtained from an arbitrary scanning angle from the scan origin. In this way, path-dependency between slices can be preserved.

Figure 5A:
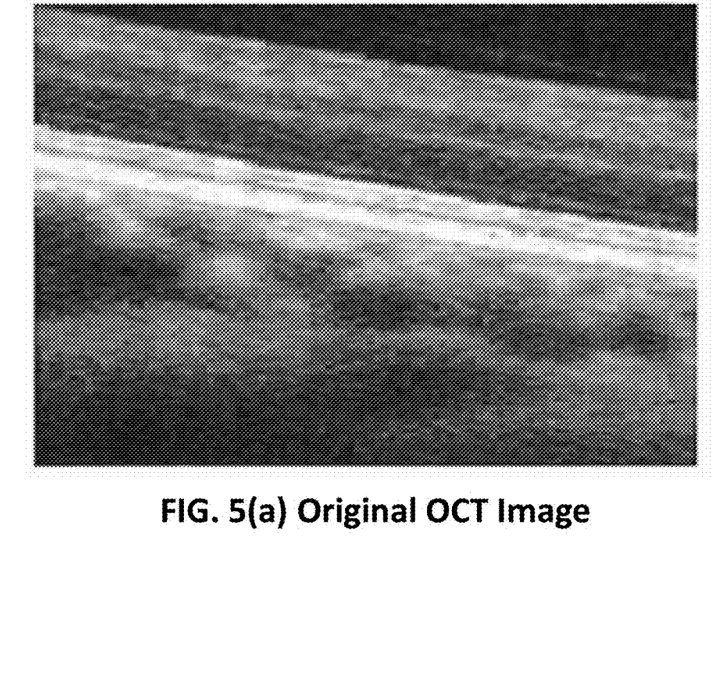
FIG. 5(a) illustrates a normal, slowly scanned OCT image
Figure 5B:
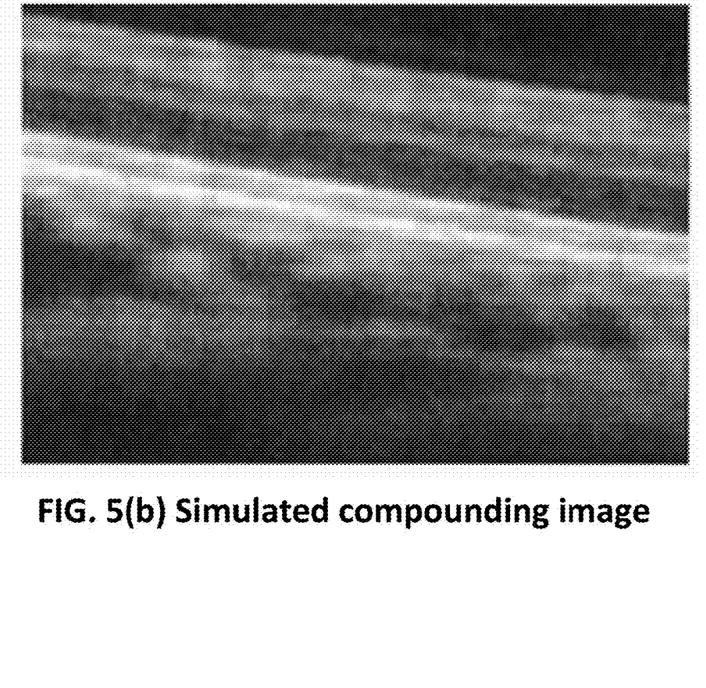
FIG. 5(b) illustrates a simulated compounding image

FIG. 5(a) and FIG. 5(b) illustrate results of the above recursive acquisition simulation. FIG. 5(a) illustrates an original OCT B-mode image, wherein the image is slowly acquired using conventional OCT. FIG. 5(b) is a simulated compounding image reconstructed using recursive data acquisition. The image dithering in FIG. 5(b) is due to the simulated scanner translation during an OCT wavelength-sweep. In both images, the interval between A-lines are a 10-pixel distance.

Figure 6:
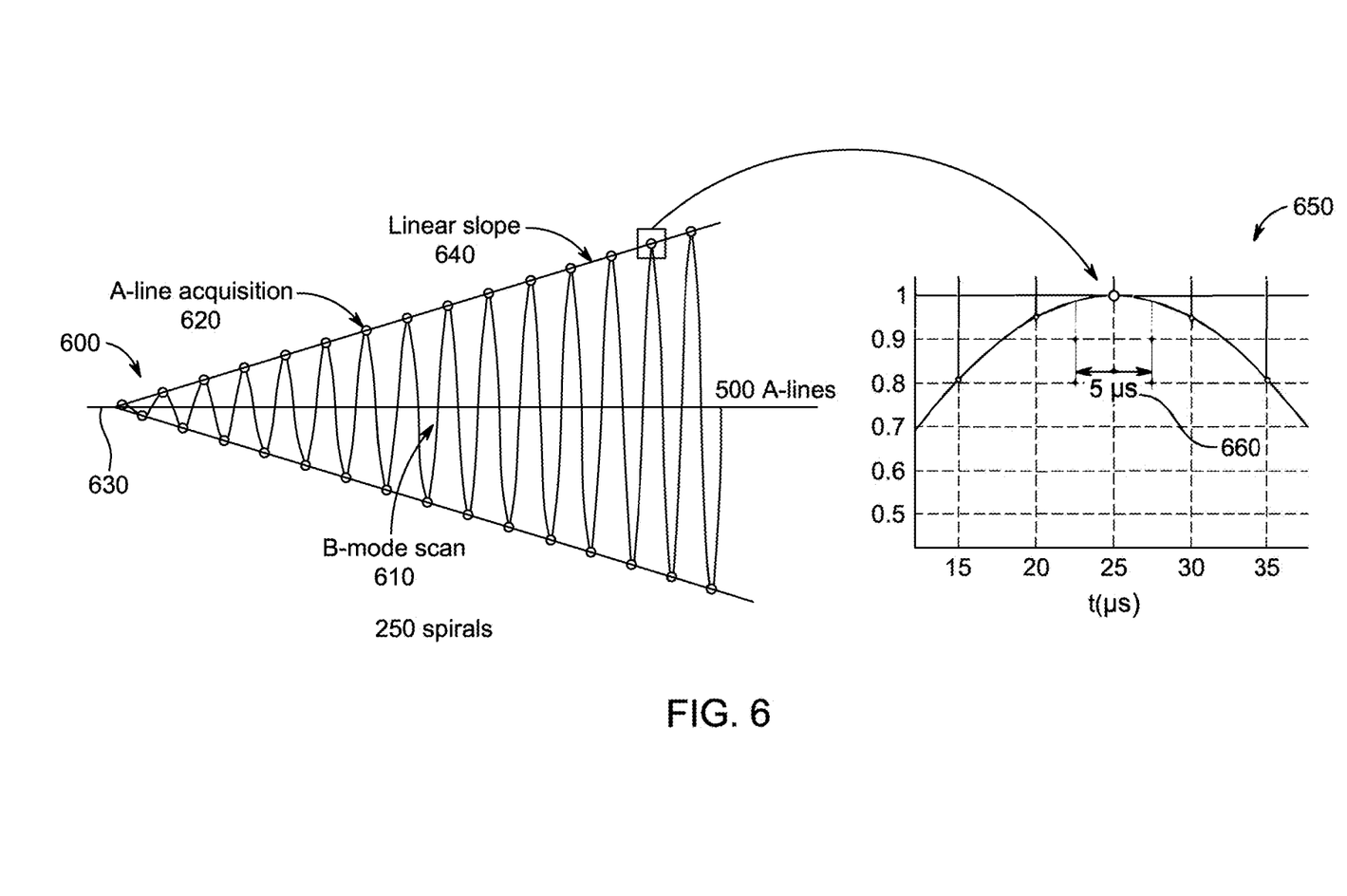
FIG. 6 illustrates the critical method to scan and acquire the OCT mode penetrating scan, during one frame of normal use for a surface RGB image.

FIG. 6 illustrates a B-mode edge scan and data acquisition scheme. The sinusoidal scanning path 600 represents the area through which a probe and its light source are driven during a linear scan. During a B-mode scan, the speed of the probe is at a maximum along center line 630, and at a minimum (i.e., zero speed) along the edge line 620 (during which A-line acquisition occurs), which has an increasing, linear slope 640. Note the slow scan motion during acquisition (i.e., 5 µSec).

In OCT scans, a slowly moving scan position during A-line acquisitions avoids distortions and smearing effects. Accordingly, in the current method, A-line data is exclusively collected at the endpoints of the B-mode scan, where the fiber scan movement is slowest while it reverses course. In this manner, data can be acquired at the most stable probe position.

The present example of FIG. 6 illustrates 250 oscillations or spirals, during the OCT B-mode scan 610 resulting in 500 A-line acquisitions along endpoints of the scanning area. In OCT B-mode scans, the radius is linearly increased as the scan travels along linear slope 640. Graph 650 enlarges a portion of an edge lie scan at a point where the A-line data is collected, and the probe movement is minimal. In an example, a conventional spectral domain OCT can take 5 µs to take an A-line spectrometer reading 660.

Figure 7:
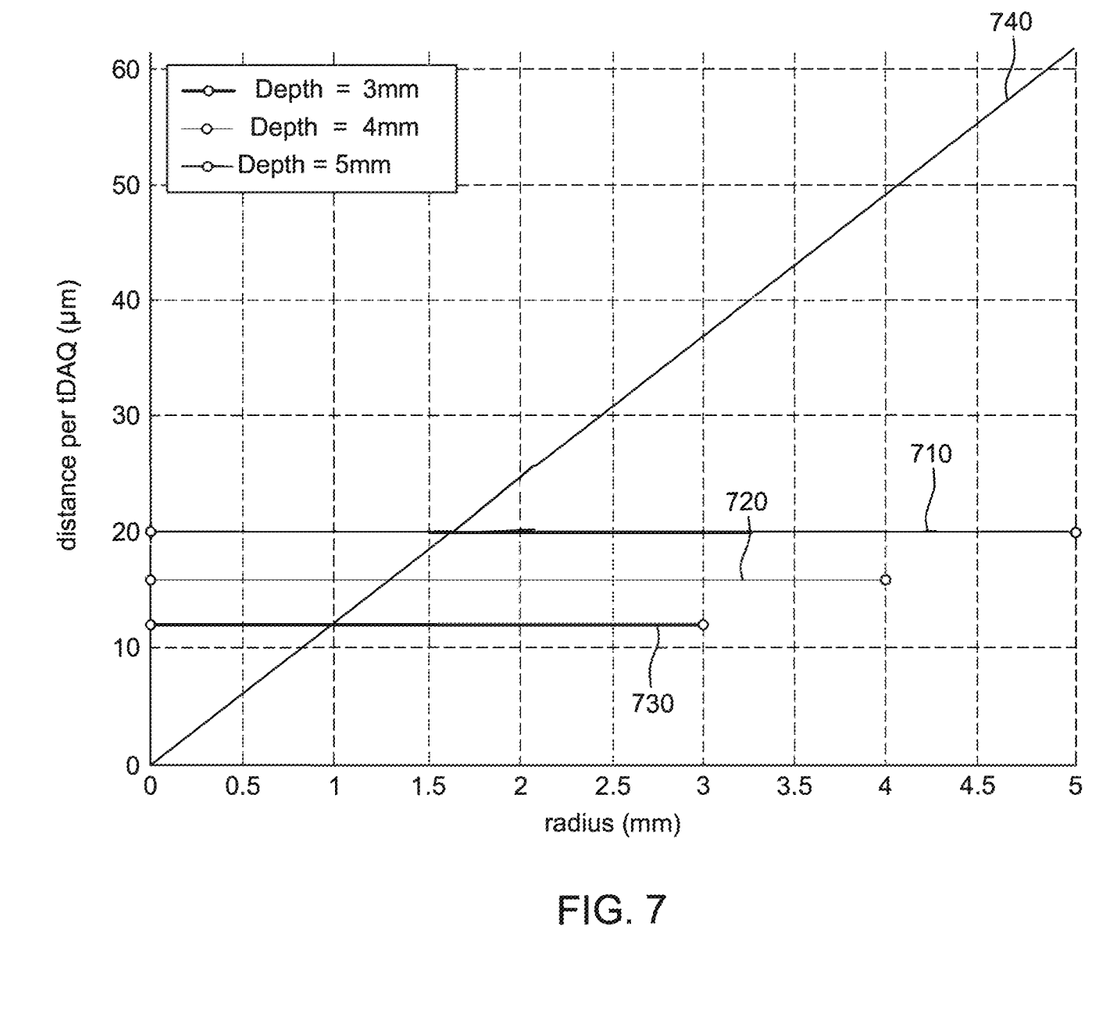
FIG. 7 illustrates a relationship between lateral resolution and a radius of a B-mode scan.
Figure 8:
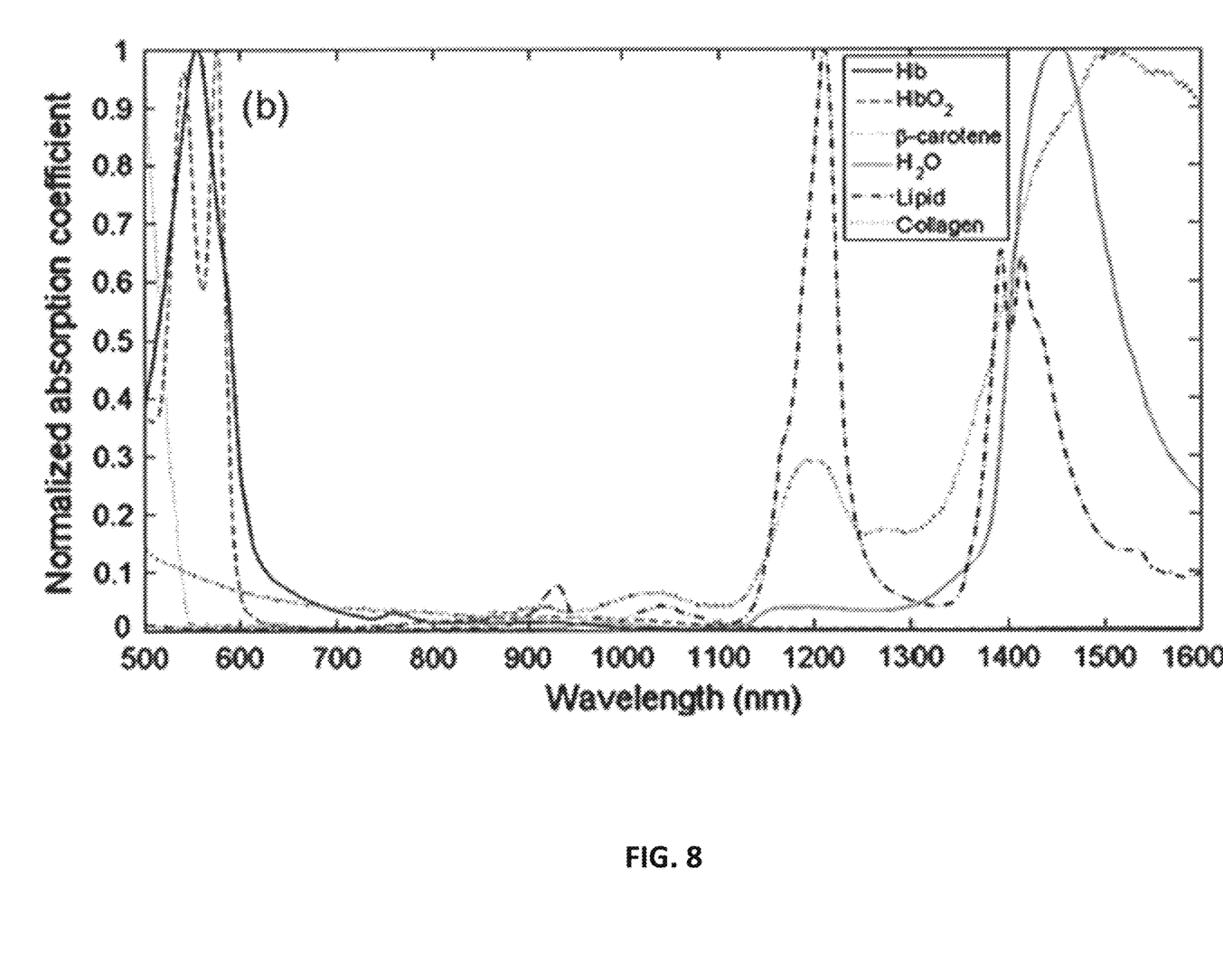
FIG. 8 illustrates absorption coefficients of tissue constituents for various wavelengths.

FIG. 7 illustrates a relationship between motion induced reduction of lateral resolution and the radius of a B-mode scan (defined as the distance between the SFE probe and an imaging surface). The X-axis represents the B-mode scan radius (mm) on the imaging surface and Y-axis represents displacement of the probe during A-line acquisition time. Line 740 represents the probe's moving distance during A-line acquisitions at each B-mode radius. For example, using a 5 microsecond acquisition window, at a 2.5 mm depth, the image would move 30 microns laterally. Horizontal lines 710, 720, 730 represent lateral resolution based on a maximum B-mode scan radius. At a depth of 5 mm, represented by 710, the motion during acquisition would be 20 microns. Similarly, at a depth of 4 mm, 720, the motion during acquisition would be approximately 15 microns, and at a depth of 3 mm, 730, the motion would be approximately 12 microns. FIG. 8 illustrates absorption coefficients of tissue constituents, applicable to various embodiments and applications of the B-mode scans and methods discussed herein. SFE transmits single mode laser lights for RGB and OCT imaging through the shared single mode fiber. The wavelengths of RGB are typically between 400-700 nm and OCT is between 900-1300 nm. The appropriate single mode fiber and OCT wavelength should be chosen to transmit both RGB and OCT in single mode without significant loss or mode changes (to multimode). FIG. 8 illustrates that in the 700-1100 nm wavelength range, the average absorption rate of materials is less than 10%, thus being particularly applicable for vascular applications.

Figure 9:
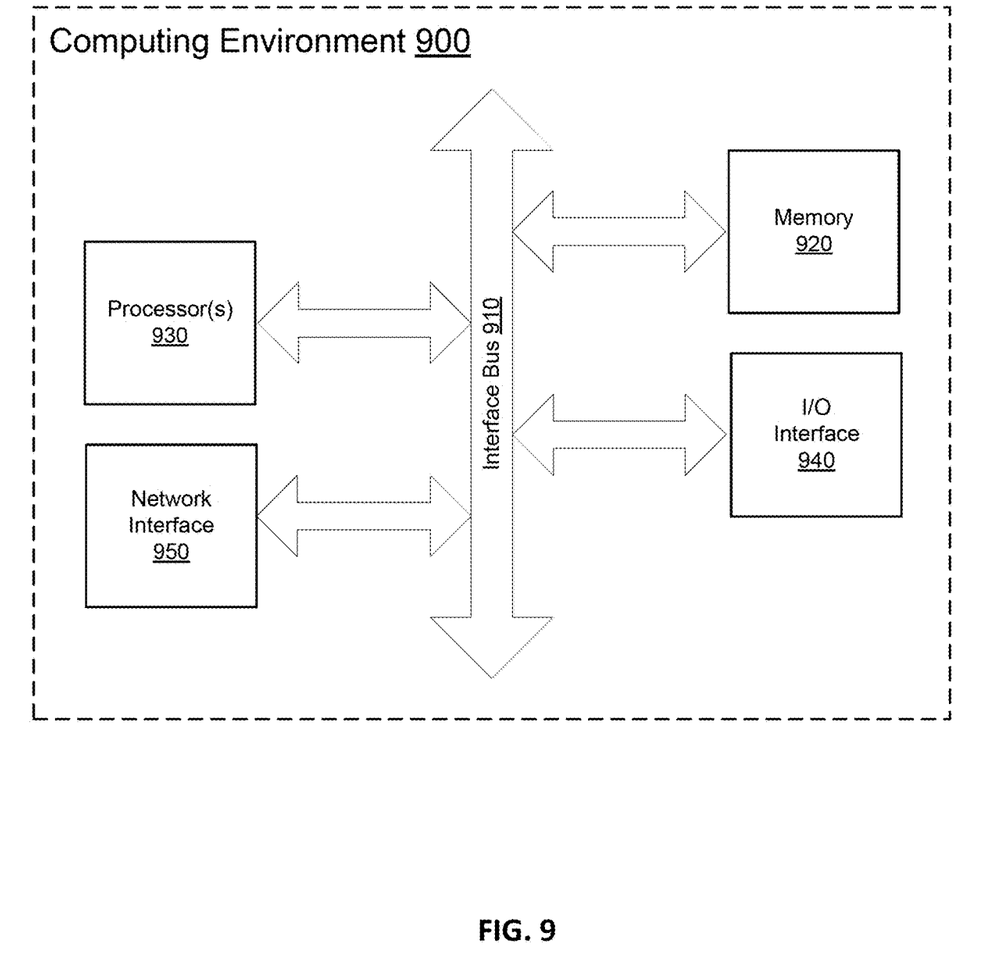
FIG. 9 illustrates an example computing environment in accordance with embodiments discussed herein.

FIG. 9 illustrates an exemplary computing environment in which embodiments of the present invention is depicted and generally referenced as computing environment 900. As utilized herein, the phrase "computing system" generally refers to a dedicated computing device with processing power and storage memory, which supports operating software that underlies the execution of software, applications, and computer programs thereon. As shown by FIG. 9, computing environment 900 includes bus 910 that directly or indirectly couples the following components: memory 920, one or more processors 930, I/O interface 940, and network interface 950. Bus 910 is configured to communicate, transmit, and transfer data, controls, and commands between the various components of computing environment 900.

Computing environment 900, such as a PC, typically includes a variety of computer-readable media. Computer-readable media can be any available media that is accessible by computing environment 900 and includes both volatile and nonvolatile media, removable and non-removable media. Computer-readable media may comprise both computer storage media and communication media. Computer storage media does not comprise, and in fact explicitly excludes, signals per se.

Computer storage media includes volatile and nonvolatile, removable and non-removable, tangible and non-transient media, implemented in any method or technology for storage of information such as computer-readable instructions, data structures, program modules or other data. Computer storage media includes RAM; ROM; EE-PROM; flash memory or other memory technology; CD-ROMs; DVDs or other optical disk storage; magnetic cassettes, magnetic tape, magnetic disk storage or other magnetic storage devices; or other mediums or computer storage devices which can be used to store the desired information, and which can be accessed by computing environment 900.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, communication media includes wired media, such as a wired network or direct-wired connection, and wireless media, such as acoustic, RF, infrared and other wireless media. Combinations of any of the above should also be included within the scope of computer-readable media.

Memory 920 includes computer-storage media in the form of volatile and/or nonvolatile memory. The memory may be removable, non-removable, or a combination thereof. Memory 920 may be implemented using hardware devices such as solid-state memory, hard drives, optical-disc drives, and the like. Computing environment 900 also includes one or more processors 930 that read data from various entities such as memory 920, I/O interface 940, and network interface 950.

I/O interface 940 enables computing environment 900 to communicate with different input devices and output devices. Examples of input devices include a keyboard, a pointing device, a touchpad, a touchscreen, a scanner, a microphone, a joystick, and the like. Examples of output devices include a display device, an audio device (e.g. speakers), a printer, and the like. These and other I/O devices are often connected to processor 910 through a serial port interface that is coupled to the system bus, but may be connected by other interfaces, such as a parallel port, game port, or universal serial bus (USB). A display device can also be connected to the system bus via an interface, such as a video adapter which can be part of, or connected to, a graphics processor unit. I/O interface 940 is configured to coordinate I/O traffic between memory 920, the one or more processors 930, network interface 950, and any combination of input devices and/or output devices.

Network interface 950 enables computing environment 900 to exchange data with other computing devices via any suitable network. In a networked environment, program modules depicted relative to computing environment 900, or portions thereof, may be stored in a remote memory storage device accessible via network interface 950. It will be appreciated that the network connections shown are exemplary and other means of establishing a communications link between the computers may be used.

It is understood that the term circuitry used through the disclosure can include specialized hardware components. In the same or other embodiments circuitry can include microprocessors configured to perform function(s) by firmware or switches. In the same or other example embodiments circuitry can include one or more general purpose processing units and/or multi-core processing units, etc., that can be configured when software instructions that embody logic operable to perform function(s) are loaded into memory, e.g., RAM and/or virtual memory. In example embodiments where circuitry includes a combination of hardware and software, an implementer may write source code embodying logic and the source code can be compiled into machine readable code that can be processed by the general purpose processing unit(s). Additionally, computer executable instructions embodying aspects of the invention may be stored in ROM EEPROM, hard disk (not shown), RAM, removable magnetic disk, optical disk, and/or a cache of processing unit. A number of program modules may be stored on the hard disk, magnetic disk, optical disk, ROM, EEPROM or RAM, including an operating system, one or more application programs, other program modules and program data. It will be appreciated that the various features and processes described above may be used independently of one another or may be combined in various ways. All possible combinations and sub-combinations are intended to fall within the scope of this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

In an embodiment, a duplex system for acquiring images may comprise a scanning fiber endoscope comprising a probe with a single mode scanning fiber resonating with cantilever resonance along electronically controlled scanning paths, and at least one computing device comprising a memory in operable communication with at least one processor, the memory having instructions to cause the at least one processor to obtain one or more RGB surface image frames from the endoscope, obtain one or more penetrating OCT cross-sectional image frames from the endoscope, and display duplex images by interleaving the one or more RGB surface image frames and interleaving the one or more OCT cross-sectional image frames.

In the embodiment, the memory may comprise instructions to further cause the at least one processor to construct a plurality of B-mode images from a plurality of A-line scans performed while obtaining the one or more RGB surface image frames, each B-mode image offset by a scanning angle. In the embodiment, wherein interleaving includes interleaving the plurality of B-mode images to construct a three-dimensional image or pre-interventional volumetric survey. In the embodiment, wherein the three-dimensional image is used to measure a volume of biological structures.

In the embodiment, wherein the single mode scanning fiber within the probe oscillates along a scanning path within a probe. In the embodiment, wherein the one or more OCT cross-section image frames identify at least one of an occlusion, a calcification, adventitia, and a microchannel.

In an embodiment, a method for acquiring OCT B-mode images may comprise oscillating a cantilever scanning fiber within a probe along a scanning path, wherein the probe is configured to obtain reflected light generated by the scanning fiber, and the oscillating scanning path increases in amplitude over time, obtaining a plurality of A-line scans from the obtained reflected light, each A-line scan obtained at a point along the oscillating scanning path where a speed of the probe is at a minimum, and constructing a B-mode image from the plurality of A-line scans.

In the embodiment, wherein the oscillating scanning path is defined by two sinusoidal inputs.

In the embodiment, further comprising constructing a plurality of B-mode images from the plurality of A-line scans, each B-mode image offset by a scanning angle. In the embodiment, further comprising interleaving the plurality of B-mode images to construct a three-dimensional image.

In the embodiment, wherein the probe is in a scanning fiber endoscope.

In an embodiment, a computer readable storage medium comprising instructions stored thereon that may cause a computing system to at least oscillate a probe along a scanning path, the probe configured to obtain reflected light generated by the probe, the scanning path increasing in amplitude over time, obtain a plurality of A-line scans from the obtained reflected light, each A-line scan obtained at a point along the scanning path where a speed of the probe is at a minimum, and construct a B-mode image from the plurality of A-line scans.

In the embodiment, further comprising instructions to cause the computing system to at least: construct a plurality of B-mode images from the plurality of A-line scans, each B-mode image offset by a scanning angle.

In the embodiment, further comprising instructions to cause the computing system to at least construct a plurality of RGB images from the reflected light obtained while the probe moves along the scanning path, and interleave the plurality B-mode images with the plurality of RGB images to construct a duplex image.

In the embodiment, wherein the B-mode image depicts an area within a blood vessel lumen.

In the embodiment, wherein the B-mode image identifies an occlusion within a blood vessel.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed:

1. A method for acquiring OCT B-mode images, comprising:
    oscillating a cantilever scanning fiber within a probe along a scanning path, wherein the probe is configured to obtain reflected light generated by the scanning fiber, and the oscillating scanning path increases in amplitude over time;
    obtaining a plurality of A-line scans from the obtained reflected light, each A-line scan obtained at a point along the oscillating scanning path that the scanning fiber reaches a minimum speed; and
    constructing a B-mode image from the plurality of A-line scans.

2. The method of claim 1, wherein the oscillating scanning path is defined by two sinusoidal inputs.

3. The method of claim 1, further comprising constructing a plurality of B-mode images from the plurality of A-line scans, each B-mode image offset by a scanning angle.

4. The method of claim 3, further comprising interleaving the plurality of B-mode images to construct a three-dimensional image.

5. The method of claim 1, further comprising:
    constructing a plurality of RGB images from the reflected light obtained while the scanning fiber moves along the oscillating scanning path.

6. The method of claim 5, further comprising
    interleaving the plurality of RGB images to create a first image of a duplex image; and
    interleaving the plurality B-mode images to create a second image of the duplex image.

7. The method of claim 1, wherein the probe is in a scanning fiber endoscope.

8. The method of claim 1, further comprising:
    analyzing the reflected light generated by the scanning fiber with an interferometer to identify an origin and a location of the reflected light.

9. The method of claim 8, further comprising:
    utilizing a reference arm to provide a reference point for the interferometer.

10. A non-transitory computer readable storage medium comprising instructions stored thereon that cause a computing system to at least:
    oscillate a cantilever scanning fiber within a probe along a scanning path, wherein the probe is configured to obtain reflected light generated by the scanning fiber, the oscillating scanning path increasing in amplitude over time;
    obtain a plurality of A-line scans from the obtained reflected light, each A-line scan obtained at a point along the oscillating scanning path where a speed of the scanning fiber is at a minimum; and
    construct a B-mode image from the plurality of A-line scans.

11. The non-transitory computer readable storage medium of claim 10, further comprising instructions to cause the computing system to at least construct a plurality of B-mode images from the plurality of A-line scans, each B-mode image offset by a scanning angle.

12. The non-transitory computer readable storage medium of claim 11, further comprising instructions to cause the computing system to at least interleave the plurality of B-mode images to construct a three-dimensional image.

13. The non-transitory computer readable storage medium of claim 11, further comprising instructions to cause the computing system to at least:
    construct a plurality of RGB images from the reflected light obtained while the scanning fiber moves along the oscillating scanning path; and
    interleave the plurality B-mode images as a first image of a duplex image and interleave the plurality of RGB images as a second image of the duplex image.

14. The non-transitory computer readable storage medium of claim 10, wherein the B-mode image depicts an area within a blood vessel lumen.

15. The computer readable storage medium of claim 10, wherein the B-mode image identifies an occlusion within a blood vessel.

16. The non-transitory computer readable storage medium of claim 10, further comprising instructions to cause the computing system to at least:
    analyze the reflected light generated by the scanning fiber with an interferometer to identify an origin and a location of the reflected light.

17. The non-transitory computer readable storage medium of claim 16, further comprising instructions to cause the computing system to at least:
    utilize a reference arm to provide a reference point for the interferometer.

* * * * *